United States Patent

Miller et al.

[19]

[11] Patent Number: 5,985,910
[45] Date of Patent: Nov. 16, 1999

[54] 3-[4-(2-PHENYL-INDOLE-1-YLMETHYL) PHENYL]- ACRYLAMIDES AS ESTROGENIC AGENTS

[75] Inventors: Chris P. Miller, Strafford; Bach D. Tran, Media, both of Pa.

[73] Assignee: American Home Products Corporation, Madison, N.J.

[21] Appl. No.: 08/837,129

[22] Filed: Apr. 14, 1997

Related U.S. Application Data

[60] Provisional application No. 60/015,646, Apr. 19, 1996.
[51] Int. Cl.$^6$ .................... A61K 31/165; C07D 209/04; C07D 209/18; C07D 233/10
[52] U.S. Cl. .................... 514/415; 514/613; 514/617; 514/619; 548/490; 548/491; 548/503; 548/511; 564/163; 564/166; 564/180
[58] Field of Search ............................. 514/415; 548/490, 548/491, 511

[56] References Cited

U.S. PATENT DOCUMENTS

| | | | |
|---|---|---|---|
| 4,943,572 | 7/1990 | von Angerer | 514/235.2 |
| 5,023,254 | 6/1991 | von Angerer | 514/235.5 |
| 5,124,335 | 6/1992 | Patchett et al. | 514/300 |
| 5,496,844 | 3/1996 | Inai et al. | 514/415 |

FOREIGN PATENT DOCUMENTS

| | | |
|---|---|---|
| 0639567 | 2/1995 | European Pat. Off. . |
| 93/10741 | 6/1993 | WIPO . |
| 93/23374 | 11/1993 | WIPO . |
| 95/17383 | 6/1995 | WIPO . |
| 96/03375 | 2/1996 | WIPO . |

OTHER PUBLICATIONS von Angerer et al., Amer. Chem. Soc., pp. 2635–2640, 1990.
von Angerer et al., Amer. Chem. Soc., pp. 132–136, 1986.
Biberger et al., J. Steroid Biochem. Molec. Biol., vol. 58, No. 1, pp. 31–43, 1996.
Henderson et al., Ann. N.Y. Aca. Sci., pp. 176, 177, 189, 1995.
Oparil "Hypertension in postmenopausal Woman:Pathology and Management" EMBASE 95:283951, 1995.
von Angerer et al., J. Med. Chem. vol. 27, pp. 1439–1447, 1984.
Biberger "2–Phenylindoles with Sulfer Containing Side Chains", CA 125:316191, 1996.

*Primary Examiner*—Johann Richter
*Assistant Examiner*—Jane C. Oswecki
*Attorney, Agent, or Firm*—Steven R. Eck

[57] ABSTRACT

The present invention relates to new 3-[4-(2-Phenyl-Indole-1-ylmethyl)-Phenyl]-Acrylamide compounds which are useful as estrogenic agents, as well as pharmaceutical compositions and methods of treatment utilizing these compounds, the compounds having the following general structure.

14 Claims, No Drawings

3-[4-(2-PHENYL-INDOLE-1-YLMETHYL) PHENYL]- ACRYLAMIDES AS ESTROGENIC AGENTS

This application claims the benefit of U.S. Provisional Application No. 60/015,646, filed Apr. 19, 1996.

The present invention relates to new 3-[4-(2-Phenyl-Indole-1-ylmethyl)-Phenyl]-Acrylamide compounds which are useful as estrogenic agents, as well as pharmaceutical compositions and methods of treatment utilizing these compounds.

BACKGROUND OF THE INVENTION

The use of hormone replacement therapy for bone loss prevention in post-menopausal women is well precedented. The normal protocol calls for estrogen supplementation using such formulations containing estrone, estriol, ethynyl estradiol or conjugated estrogens isolated from natural sources (Premarin from Wyeth-Ayerst). In some patients, therapy may be contraindicated due to the proliferative effects unopposed estrogens (estrogens not given in combination with progestins) have on uterine tissue. This proliferation is associated with increased risk for endometriosis and/or endometrial cancer. The effects of unopposed estrogens on breast tissue is less clear, but is of some concern. The need for estrogens which can maintain the bone sparing effect while minimizing the proliferative effects in the uterus and breast is evident. Certain nonsteroidal antiestrogens have been shown to maintain bone mass in the ovariectomized rat model as well as in human clinical trials. Tamoxifen, for example, is a useful palliative for the treatment of breast cancer. It has been demonstrated to exert an estrogen agonist like effect on the bone, in humans. However, it is also a partial agonist in the uterus and this is cause for some concern. Raloxifene, a benzothiophene antiestrogen, has been shown to stimulate uterine growth in the ovariectomized rat to a lesser extent than Tamoxifen while maintaining the ability to spare bone. A suitable review of tissue selective estrogens is: Tissue -Selective Actions Of Estrogen Analogs, *Bone* Vol. 17, No. 4, October 1995, 181S–190S.

The use of indoles as estrogen antagonists has been reported by Von Angerer, Chemical Abstracts, Vol. 99, No. 7 (1983), Abstract No. 53886u. Also, see, J.Med.Chem. 1990, 33, 2635–2640; J.Med.Chem. 1987, 30, 131–136. Also see Ger. Offen., DE 3821148 A1 891228. Additionally, see WO, A, 93 23374 (Otsuka Pharmaceutical Factory, Inc.). Von Angerer's work is limited to aliphatic chains linked to the indole nitrogen and then linked to the basic amine (or amide) or, benzyl groups not possessing the basic amine. The world patent from Otsuka (Japanese) consists of compounds related to the present invention except $R_3$ (as shown in formula I) is defined as —SR where R is alkyl. Additionally, there are no chains from the indole nitrogen in their patent with the same structure as the ones given in the present invention, either by claim or example. A related patent WO A 93 10741 describes 5-Hydroxyindoles. WO A 95 17383 (Kar Bio AB) describes aliphatic chain compounds.

DESCRIPTION OF THE INVENTION

Compounds of the general structure type shown in formulas (I) and (II) are estrogen agonists/antagonists useful for the trement of diseases associated with estrogen deficiency. The compounds of the present invention show strong binding to the estrogen receptor. These compounds have proven to be antiestrogens with little intrinsic estrogenicity. In a three-day ovariectimized rat model, compounds of formula (I) are capable of antagonizing the effects of 17β-estradiol while showing little uterine stimulation when dosed alone.

The present invention includes compounds of formulas (I) or (II), below:

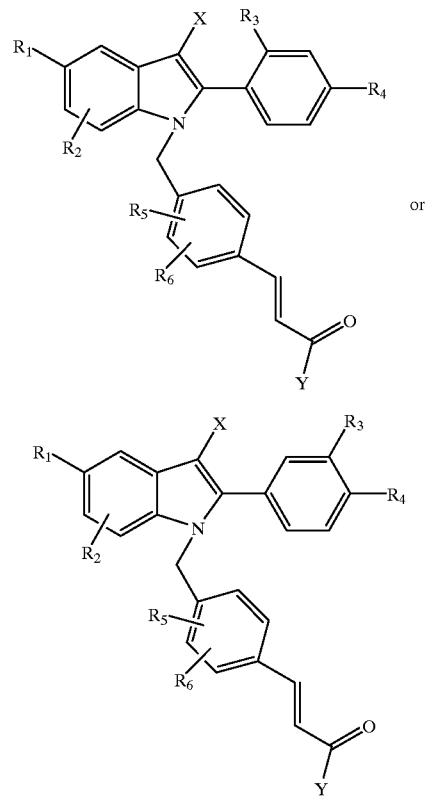

wherein:
  $R_1$ is selected from H, OH or the $C_1$–$C_4$ esters or alkyl ethers thereof, or halogen;
  $R_2$, $R_3$, $R_4$, $R_5$, and $R_6$ are independently selected from H, OH or the $C_1$–$C_4$ esters or alkyl ethers thereof, halogen, cyano, $C_1$–$C_6$ alkyl, or trifluoromethyl, with the proviso that, when $R_1$ is H, $R_2$ is not OH;
  X is selected from H, $C_1$–$C_6$ alkyl, cyano, nitro, trifluoromethyl, halogen;
  Y is selected from:
  a) the moiety:

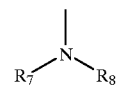

wherein $R_7$ and $R_8$ are independently selected from the group of H, $C_1$–$C_6$ alkyl, phenyl
  b) a five-membered saturated, unsaturated or partially unsaturated heterocycle containing up to two heteroatoms selected from the group consisting of —O—, —NH—, —N($C_1C_4$ alkyl)—, —N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$—, —CN—, —$CONHR_1$—, —$NH_2$—, $C_1$–$C_4$ alkylamino, di($C_1$–$C_4$)alkylamino, —$NHSO_2R_1$—, —$NHCOR_1$—, —$NO_2$—, and phenyl substituted with 1–3 ($C_1$–$C_4$)alkyl;

c) a six-membered saturated, unsaturated or partially unsaturated heterocycle containing up to two heteroatoms selected from the group consisting of —O—, —NH—, —N($C_1C_4$ alkyl)—, —N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$—, —CN—, —$CONHR_1$—, —$NH_2$—, $C_1$–$C_4$ alkylamino, di($C_1$–$C_4$)alkylamino, —$NHSO_2R_1$—, —$NHCOR_1$—, —$NO_2$, and phenyl substituted with 1–3 ($C_1$–$C_4$)alkyl;

d) a seven-membered saturated, unsaturated or partially unsaturated heterocycle containing up to two heteroatoms selected from the group consisting of —O—, —NH—, —N($C_1C_4$ alkyl)—, —N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$—, —CN—, —$CONHR_1$—, —$NH_2$—, $C_1$–$C_4$ alkylamino, di($C_1$–$C_4$)alkylanino, —$NHSO_2R_1$—, —$NHCOR_1$—, —$NO_2$—, and phenyl substituted with ($C_1$–$C_4$)alkyl; or e) a bicyclic ring system consisting of a five or six-membered heterocyclic ring fused to a phenyl ring, said heterocyclic ring containing up to two heteroatoms selected from the group of —O—, —NH—, —N($C_1C_4$ alkyl)—, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$—, —CN—, —$CONHR_1$—, —$NH_2$—, $C_1$–$C_4$ alkylamino, di($C_1$–$C_4$)alkylamino, —$NHSO_2R_1$—, —$NHCOR_1$, —$NO_2$, and phenyl substituted with 1–3 ($C_1$–$C_4$)alkyl.

The more preferred compounds of this invention are those having the general structures I or II, above, wherein:

$R_1$ is selected from H, OH or the $C_1$–$C_4$ esters or alkyl ethers thereof, halogen;

$R_2$, $R_3$, $R_4$, $R_5$, and $R_6$ are independently selected from H, OH or the $C_1$–$C_4$ esters or alkyl ethers thereof, halogen, cyano, $C_1$–$C_6$ alkyl, or trifluoromethyl, with the proviso that, when $R_1$ is H, $R_2$ is not OH;

X is selected from H, $C_1$–$C_6$ alkyl, cyano, nitro, trifluoromethyl, halogen;

Y is the moiety

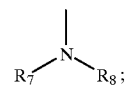

$R_7$ and $R_8$ are selected independently from H, $C_1$–$C_6$ alkyl, or combined by —$(CH_2)p$—, wherein p is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$), —$NH_2$, $C_1$–$C_4$ alkylamino, $C_1$–$C_4$ dialkylamino, —$NHSO_2(C_1$–$C_4)$, —NHCO ($C_1$–$C_4$), and —$NO_2$.

The rings formed by a concatenated $R_7$ and $R_8$, mentioned above, may include, but are not limited to, aziridine, azetidine, pyrrolidine, piperidine, or hexamethyleneamine rings.

It is further preferred that, when $R_7$ and $R_8$ are concatenated together, the ring so formed is optionally substituted with 1–3 substituents selected from a group containing $C_1$–$C_3$ alkyl, trifluoromethyl, halogen, hydrogen, phenyl, nitro, —CN.

The compounds of the invention are partial estrogen agonists and display high affinity for the estrogen receptor. Unlike many estrogens, however, these compounds do not cause increases in uterine wet weight. These compounds are antiestrogenic in the uterus and can completely antagonize the trophic effects of estrogen agonists in uterine tissue. These compounds are useful in treating or preventing mammal disease states or syndromes which are caused or associated with an estrogen deficiency.

The present compounds have the ability to behave like estrogen agonists by lowering cholesterol and preventing bone loss. Therefore, these compounds are useful for treating many maladies including osteoporosis, prostatic hypertrophy, infertility, breast cancer, endometrial cancer, cardiovascular disease, contraception, Alzheimer's disease and melanoma. Additionally, these compounds can be used for hormone replacement therapy in post-menopausal women or in other estrogen deficiency states where estrogen supplementation would be beneficial.

The compounds of this invention may also be used in methods of treatment for bone loss, which may result from an imbalance in an individual's formation of new bone tissues and the resorption of older tissues, leading to a net loss of bone. Such bone depletion results in a range of individuals, particularly in post-menopausal women, women who have undergone hysterectomy, those receiving or who have received extended corticosteroid therapies, those experiencing gonadal dysgenesis, and those suffering from Cushing's syndrome. Special needs for bone replacement can also be addressed using these compounds in individuals with bone fractures, defective bone structures, and those receiving bone-related surgeries and/or the implantation of prosthesis. In addition to those problems described above, these compounds can be used in treatments for osteoarthritis, Paget's disease, osteomalacia, osteohalisteresis, endometrial cancer, multiple myeloma and other forms of cancer having deleterious effects on bone tissues. Methods of treating the maladies listed herein are understood to comprise administering to an individual in need of such treatment a pharmaceutically effective amount of one or more of the compounds of this invention or a pharmaceutically acceptable salt thereof. This invention also includes pharmaceutical compositions utilizing one or more of the present compounds, and/or the pharmaceutically acceptable salts thereof, along with one or more pharmaceutically acceptable carriers, excipients, etc.

It is understood that the dosage, regimen and mode of administration of these compounds will vary according to the malady and the individual being treated and will be subjected to the judgment of the medical practitioner involved. It is preferred that the administration of one or more of the compounds herein begins at a low dose and be increased until the desired effects are achieved.

Effective administration of these compounds may be given at a dose of from about 0.1 mg/day to about 1,000 mg/day. Preferably, administration will be from about 50 mg/day to about 600 mg/day in a single dose or in two or more divided doses. Such doses may be administered in any manner useful in directing the active compounds herein to the recipient's bloodstream, including orally, parenterally (including intravenous, intraperitoneal and subcutaneous injections), and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystale cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

Compounds of this invention can be synthesized in a general sense according to Scheme 1.

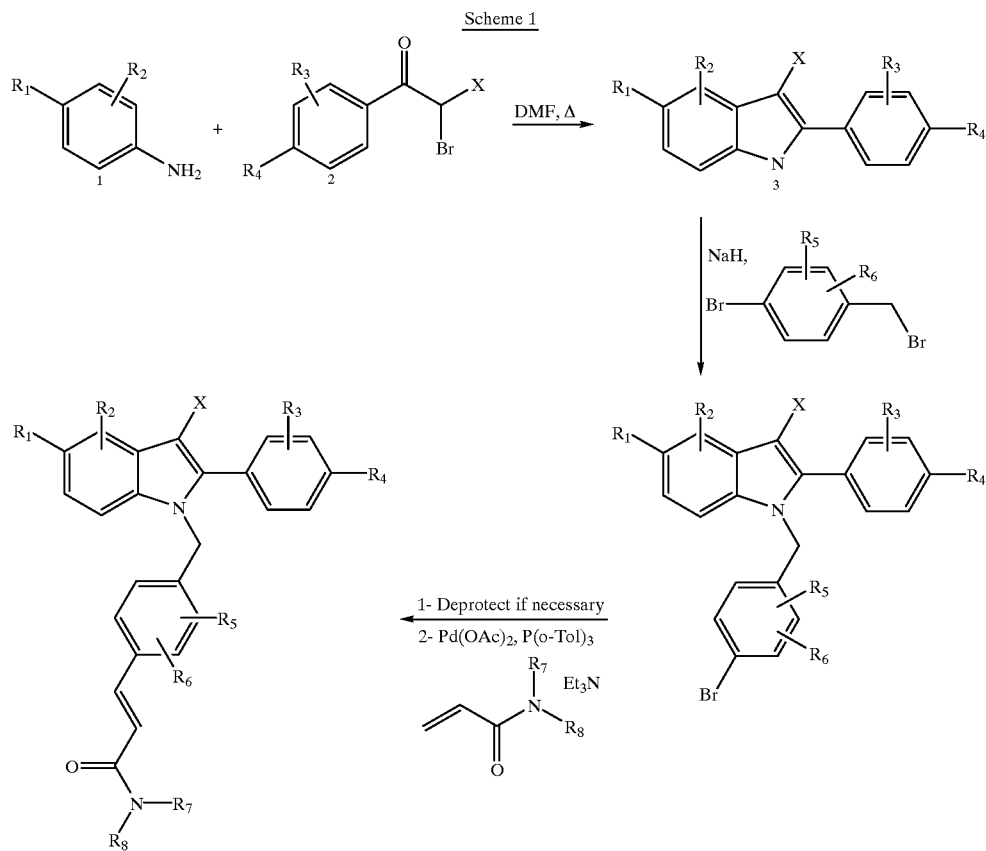

The initial indole synthesis is accomplished by heating an appropriately substituted aniline (1) with an appropriately substituted alphabromophenylpropriophenone (2) in a suitably high boiling solvent such as DMF. The product is then alkylated with a 4-bromobenzyl bromide to give the substituted indole (3). At this point, deprotection of phenols (if present) is done. Normally, the phenols are protected as benzyl ethers and can conveniently be cleaved with TMSI. The acrylamides are coupled using Heck reaction conditions in either neat $Et_3N$ or $Et_3N/CH_3CN$.

Solvents used for reactions were anhydrous Aldrich Sure Seal™ without further purification. Reagents were typically Aldrich and used without further purification. All reactions were carried out under a nitrogen atmosphere. Chromatography was performed using 230–400 mesh silica gel (Merck Grade 60, Aldrich Chemical Company). Thin layer chromatography was performed with Silica Gel 60 $F_{254}$ plates from EM Science. $^1H$ NMR spectra were obtained on a Bruker AM-400 instrument in DMSO and chemical shifts reported in ppm. Melting points were determined on a Thomas-Hoover apparatus and are uncorrected. IR spectra were recorded on a Perkin-Elmer diffraction grating or Perkin-Elmer 784 spectrophotometers. Mass spectra were recorded on a Kratos MS 50 or Finnigan 8230 mass spectrometers. Elemental analyses were obtained with a Perkin-Elmer 2400 elemental analyzer. Analysis values are within 0.4% of theoretical.

EXAMPLE 1

5-Benzyloxy-2-(4-benzyloxy-phenyl)-3-methyl-1H-indole

A flask was charged with 4-benzyloxyaniline (45 g, 0.23 mol), 4'-benzyloxy-2-bromophenylpropiophenone (21 g, 0.066 mol), and DMF (50 mL). The reaction was heated at reflux for 30 minutes and then cooled to rt and then partitioned between EtOAc (250 mL) and 1 N HCl (aq) (100 mL). The EtOAc was washed with $NaHCO_3$ (aq) and brine, dried over $MgSO_4$. The solution was concentrated and the residue taken up in $CH_2Cl_2$ and hexanes added to precipitate out 25 g of a crude solid. The solid was dissolved in $CH_2Cl_2$ and evaporated onto silica gel and chromatographed using $CH_2Cl_2$/Hexane (1:5) to yield 9.2 g of a tan solid (33%): Mpt=150–152° C.; $^1H$ NMR (DMSO) 10.88 (s, 1 H), 7.56 (d, 2 H, J=8.8 Hz), 7.48 (d, 4 H, J=7.9 Hz), 7.42–7.29 (m, 6 H), 7.21 (d, 1 H, J=7.0 Hz), 7.13 (d, 2 H, J=8.8 Hz), 7.08 (d, 1 H, J=2.2 Hz), 6.94 (dd, 1 H, J=8.8, 2.4 Hz), 5.16 (s, 2 H), 5.11 (s, 2 H), 2.33 (s, 3 H); IR (KBr) 3470, 2880, 2820, 1620 cm$^{-1}$; MS eI m/z 419.

EXAMPLE 2

5-Benzyloxy-2-(4-fluoro-phenyl)-3-methyl-1H-indole

The title compound was prepared similarly to (3): MP=132° C.; $^1H$ NMR (DMSO) 11.0 (s, 1 H), 7.68–7.64 (m, 2 H), 7.49–7.47 (m, 2 H), 7.41–7.31 (m, 5 H), 7.23 (d, 1 H, J=8.8 Hz), 7.10 (d, 1 H, J=2.4 Hz), 6.82 (dd, 1 H, J=8.8, 2.4 Hz), 5.11 (s, 2 H), 2.34 (s, 3 H); MS EI m/z 331; CHN calcd for $C_{22}H_{18}FNO$.

EXAMPLE 3

5-Benzyloxy-2-(4-benzyloxy-phenyl)-3-methyl-1-ylmethyl-(4-phenylbromide)-indole

A solution of 60% NaH (0.17 g, 7.1 mmol) in DMF (20 mL) was cooled to 0° C. and treated by dropwise addition of benzyloxyindole 1 (2.5 g, 5.94 mmol) in DMF (10 mL). After 15 min, 4'-bromobenzylbromide (1.63 g, 6.53 mmol) in DMF (10 mL) was added dropwise. The reaction was stirred for 5 min at 0° C. and then at rt for an additional 20 min. The reaction mixture was diluted with ether (300 mL) and washed with $NH_4Cl$ (2×25 mL) then $NaHCO_3$ (1×25 mL), and brine (25 mL). The organic extracts were dried over $MgSO_4$ and concentrated. The residue was crystallized from THF/Hexanes to yield 2.7 g (77%) of 2: Mp=144–146° C.; $^1H$ NMR (CDCl$_3$) 7.51–7.36 (m, 8 H), 7.34 (d, 4 H, J=8.6 Hz), 7.20 (d, 2 H, J=8.8 Hz), 7.15 (d, 1 H, J=2.4 Hz), 7.03–7.00 (m, 3 H), 6.89 (dd, 1 H, J=8.8, 2.4 Hz), 6.80 (d, 2 H, J=8.6 Hz), 5.14 (s, 2 H), 5.12 (s, 2 H), 5.09 (s, 2 H), 2.25 (s, 3 H); IR (KBr) 3400, 3020, 1600 cm$^{-1}$; MS eI m/z 587.

EXAMPLE 4

5-Benzyloxy-2-(4-fluoro-phenyl)-3-methyl-1-ylimethyl-(4-phenylbromide)-indole

The title compound was prepared similarly to compound 5. Mp=139–139.5° C.; 1H NMR (DMSO) 7.49–7.46 (m, 2 H), 7.41–7.37 (m, 6 H), 7.33–7.27 (m, 4 H), 7.24 (d, 1 H, J=8.8 Hz), 7.16 (d, 1 H, J=2.2 Hz), 6.84 (dd, 1 H, J=8.8, 2.4 Hz), 6.73 (d, 1 H, J=8.6 Hz), 5.2 (s, 2 H), 5.12 (s, 2 H), 2.15 (s, 3 H); IR (KBr) 2920, 1630 cm$^{-1}$; MS eI m/z (499/501, Br present); CHN calcd for $C_{29}H_{23}BrFNO$.

EXAMPLE 5

2-(4-hydroxylhenyl)-3-methyl-1-ylmethyl-(4-phenylbromide)-indole-5-ol

A solution consisting of 5 (0.5 g, 0.85 mmol) in $CH_2Cl_2$ (10 mL) was treated with by dropwise addition of 3.5 eq TMSI (0.47 mL, 3.0 mmol) at rt. After a couple hours, the reaction stopped so an additional 2.2 eq TMSI was added and the reaction heated to reflux for 5 h. The reaction was cooled to 0° C. and methanol slowly added to quench the reaction. The reaction was diluted with ether (25 mL) and washed with $NaHCO_3$(25 mL), 10% $Na_2SO_3$ (25 mL), and brine. The ether layer was dried over $MgSO_4$ and concentrated onto silica gel. Chromatography with EtOAc/Hexanes (1:4 to 1:1) yielded 0.25 g 3 (71%): Mp=83–86° C.; $^1H$ NMR (CDCl$_3$) 2 H's from phenols broad (>10),s 7.35 (d, 2 H, J=9.0 Hz), 7.15 (d, 2 H, J=8.8 Hz), 7.01 (dd, 1 H, J=2.4, 0.4 HZ), 6.86 (d, 2 H, J=8.8 HZ), 6.80 (d, 1 H, J=8.6 Hz), 6.72 (dd, 1 H, J=8.6, 2.4 Hz), 5.10 (s, 2 H), 4.88 (s, 1 H), 4.50 (s, 1 H), 2.21 (s, 3 H); MS eI m/z 407/409 contains Br, IR 3390, 2900, 1600 cm$^{-1}$; CHN calc'd for $C_{22}H_{18}BrNO_2$+ 0.25 EtOAc.

EXAMPLE 6

2-(4-fluoro-phenyl)-3-methyl-1-ylmethyl-(4-phenylbromide)-indole-5-ol

The title compound was prepared similarly to compound 7 and isolated as a foam. $^1H$ NMR (DMSO) 8.79 (s, 1 H), 7.39–7.34 (m, 4 H), 7.32–7.30 (m, 3 H), 7.11 (d, 1 H, J=8.8 Hz), 6.85 (d, 1 H, J=2.2 Hz), 6.74 (d, 1 H, J=2.4 Hz), 6.63 (dd, 1 H, J=8.6, 2.2 Hz), 5.16 (s, 2 H), 2.11 (s, 3 H); IR (KBr) 3400, 2900, 1630 cm$^{-1}$; MS eI m/z 409/411 contains Br.

General Procedure For Indole Acrylamides

A solution of example 3 in $Et_3N$ is treated with tri-o-tolylphosphine (10 mol %), and acrylamide (1.25 eq) is purged thoroughly with $N_2$ and Pd(OAc)$_2$ (2.5 mol %) added. The reaction is heated at 100–110° C. in a sealed tube until completed by TLC analysis. The crude reaction product is concentrated down and either crystallized directly or chromatographed on silica gel.

EXAMPLE 7

(E)-N,N-Diethyl-3-{4-[5-hydroxy-2-(4-hydroxy-phenyl)-3-methyl-indol-1-ylmethyl]-phenyl}-acrylamide Mp=160–165° C.; $^1$H NMR 9.67 (s, 1 H), 8.72 (s, 1 H), 7.50 (d, 2 H, J=8.1 Hz), 7.37 (d, 1 H, J=15.4 Hz), 7.17 (d, 2 H, J=8.3 Hz), 7.06 (d, 1 H, J=8.8 Hz), 6.97 (d, 2 H, J=15.4 Hz), 6.86–6.82 (m, 5 H), 6.58 (dd, 1 H, J=8.6, 2.2 Hz), 5.19 (br s, 2 H), 3.47–3.42 (m, 2 H), 3.34–3.30 (m, 2 H), 2.09 (s, 3 H), 1.10 (t, 3 H, J=7.0 Hz), 1.03 (t, 3 H, J=7.0 Hz); IR (KBr) 3300, 2950, 1660, 1580 cm$^{-1}$; MS (eI) m/z 454; CHN calc'd for $C_{29}H_{30}N_2O_3$+0.15 $CH_2Cl_2$+0.30 $H_2O$.

EXAMPLE 8

1(E)-N-tert-butyl-3-{4-[5-hydroxy-2-(4-hydroxy-phenyl)-3-methyl-indol-1-ylmethyl]-phenyl}-acrylamide Mp=168–170° C.; $^1$H NMR 9.66 (s, 1 H), 8.71 (s, 1 H), 7.66 (s, 1 H), 7.34 (d, 2 H, J=8.3 Hz), 7.24 (d, 1 H, J=15.8 Hz), 7.15 (d, 2 H, J=8.3 Hz), 7.05 (d, 1 H, J=8.6 Hz), 6.85–6.82 (m, 5 H), 6.59–6.56 (m, 1 H), 6.55 (d, 1 H, J=16.0 Hz), 5.18 (s, 2 H), 2.11 (s, 3 H), 1.28 (s, 9 H); IR (KBr) 3350, 2950, 1660, 1620; MS (eI) m/z 454; CHN calc'd for $C_{29}H_{30}N_2O_3$+0.4$H_2O$

EXAMPLE 9

(E)-Pyrrolidino-3-{4-[5-hydroxy-2-(4-hydroxy-phenyl)-3-methyl-indol-1-ylmethyl]-phenyl}-acrylamide Mp=170–175° C.; $^1$H NMR 9.67 (s, 1 H), 8.71 (s, 1 H), 7.49 (d, 2 H, J=8.1 Hz), 7.35 (d, 1 H, J=15.4 Hz), 7.16 (d, 2 H, J=8.6 Hz), 7.05 (d, 1 H, J=8.8 Hz), 6.88–6.81 (m, 6 H), 6.57 (dd, 1 H, J=8.6, 2.2 Hz), 5.19 (br s, 2 H), 3.56 (t, 2 H, J=6.6 Hz), 3.35 (m, 2 H), 2.11 (s, 3 H), 1.87 (p, 2 H, J=7.0 Hz), 1.77 (p, 2 H, J=7.0 Hz); MS m/z 452; CHN calc'd for $C_{29}H_{28}N_2O_3$+0.1 MeOH+1.3 $H_2O$.

EXAMPLE 10

(E)-N,N-Dimethyl-3-{4-[5-hydroxy-2-(4-hydroxy-phenyl)-3-methyl-indol-1-ylmethyl]-phenyl}-acrylamide Mp=278–280° C.; $^1$H NMR (DMSO) 9.65 (s, 1 H), 8.70 (s, 1 H), 7.50 (d, 2 H, J=8.1 Hz), 7.33 (d, 1 H, J=15.4 Hz), 7.15 (d, 2 H, J=8.6 Hz), 7.07 (d, 1 H, J=15.6 Hz), 7.05 (d, 1 H, J=8.8 Hz), 6.85–6.80 (m, 5 H), 6.57 (dd, 1 H, J=8.6, 2.4 Hz), 5.19 (s, 2 H), 3.09 (s, 3 H), 2.88 (s, 3 H), 2.11 (s, 3 H); MS eI m/z 426; IR (KBr) 3410, 3220, 1650, 1580 cm$^{-1}$; CHN calc'd for $C_{27}H_{26}N_2O_3$+0.5 $H_2O$.

EXAMPLE 11

(E)-N,N-Dibutyl-3-{4-[5-hydroxy-2-(4-hydroxy-phenyl)-3-methyl-indol-1-ylmethyl]-phenyl}-acrylamide Mp=126–128° C., $^1$H NMR (DMSO) 9.65 (s, 1 H), 8.70 (s, 1 H), 7.48 (d, 2 H, J=8.3 Hz), 7.36 (d, 1 H, J=15.2 Hz), 7.16 (d, 2 H, J=8.6 Hz), 7.05 (d, 1 H, J=8.6 Hz), 6.97 (d, 1 H, J=15.2 Hz), 6.86–6.81 (m, 5 H), 6.57 (dd, 1 H, J=8.8, 2.4 Hz), 5.19 (s, 2 H), 3.39 (t, 2 H, J=7.0 Hz), 3.29 (t, 2 H, J=7.2 Hz), 2.11 (S, 3 H), 1.48–1.43 (M, 4 H), 1.29–1.20 (M, 4 H), 0.87 (t, 6 H, J=7.2 Hz); MS eI m/z 510; IR (KBr) 3300, 2920, 2900, 2850, 1650, 1625, 1580 cm$^{-1}$; CHN calc'd for $C_{33}H_{38}N_2O_3$.

EXAMPLE 12

(E)-N-Butyl. N'-methyl-3-{4-[5-hydroxy-2-(4-hydroxy-phenyl)-3-methyl-indol-1-ylmethyl]-phenyl}-acrylamide Mp=240–242° C.; $^1$H NMR (DMSO) 9.66 (s, 1 H), 8.70 (s, 1 H), 7.50 (d, 2 H, J=8.1 Hz), 7.38–7.32 (m, 1 H), 7.16 (d, 2 H, J=6.8 Hz), 7.06–7.01 (m, 2 H), 6.85–6.81 (m, 5 H), 6.57 (dd, 1 H, J=8.6, 2.2 Hz), 5.19 (s, 2 H), 3.44, 3.33 (2 t, 2 H, J=7.2 Hz), 3.06, 2.87 (2 s, 3 H), 2.11 (s, 3 H), 1.45 (m, 2 H), 1.24 (p, 2 H, J=7.5 Hz), 0.87 (t, 3 H, J=7.2 Hz); Ms eI m/z 468; IR (KBr) 3300, 1660, 1590 cm$^{-1}$; CHN calc'd for $C_{30}H_{32}N_2O_3$+0.2 $H_2O$.

EXAMPLE 13

(E)-Morpholino-3-{4-[5-hydroxy-2-(4-hydroxy-phenyl)-3-methyl-indol-1-ylmethyl]-phenyl}-acrylamide Mp=165–167° C., $^1$H NMR (DMSO) 9.66 (s, 1 H), 8.71 (s, 1 H), 7.52 (d, 2 H, J=8.1 Hz), 7.39 (d, 1 H, J=15.4 Hz), 7.15 (d, 2 H, J=8.6 Hz), 7.12 (d, 1 H, J=15.4 Hz), 7.06 (d, 1 H, J=8.6 Hz), 6.85–6.81 (m, 5 H), 6.57 (dd, 1 H, J=8.6, 2.2 Hz), 5.19 (s, 2 H), 3.65–3.64 (m, 2 H), 3.59–3.53 (m, 6 H), 2.11 (s, 3 H); IR (KBr) 3330, 1650, 1620, 1580 cm−1; MS (FAB) m/z 469 (M+H$^+$); CHN calc'd for $C_{29}H_{28}N_2O_4$+0.5 $H_2O$.

EXAMPLE 14

(E)-3-{4-[5-hydroxy-2-(4-hydroxy-phenyl)-3-methyl-indol-1-ylmethyl]-phenyl}-acrylamide Mp=161–163° C., $^1$H NMR (DMSO) 9.65 (s, 1 H), 8.70 (s, 1 H), 7.48 (s, 1 H), 7.37 (d, 2 H, J=8.35 Hz), 7.30 (d, 1 H, J=15.8 Hz), 7.14 (d, 2 H, J=8.35 Hz), 7.04 (d, 2 H, J=8.6 Hz), 6.85–6.81 (m, 5 H), 6.57 (dd, 1 H, J=8.8, 2.4 Hz), 6.48 (d, 1 H, J=15.8 Hz), 5.18 (s, 2 H), 2.10 (s, 3 H); IR (KBr) 3320, 3180, 1660, 1580 cm$^{-1}$; MS (FAB) m/z 399 (M+H$^+$); CHN calc'd for $C_{25}H_{22}N_2O_3$+1.3 $H_2O$.

EXAMPLE 15

(E)-N,Methyl-3-{4-[5-hydroxy-2-(4-hydroxy-phenyl)-3-methyl-indol-1-ylmethyl]-phenyl}-acrylamide Mp=155–158° C.; $^1$H NMR (DMSO) 9.64 (s, 1 H), 8.70 (s, 1 H), 7.99 (q, 1 H, J=4.4 Hz), 7.37 (d, 2 H, J=8.1 Hz), 7.30 (d, 1 H, j=15.8 Hz), 7.14 (d, 2 H, J=8.6 Hz), 7.03 (d, 1 H, J=8.6 Hz), 6.85–6.81 (m, 5 H), 6.57 (dd, 1 H, J=8.6, 2.4 Hz), 6.48 (d, 1 H, J=15.8 Hz), 5.18 (s, 2 H), 2.66 (d, 3 H, J=4.6 Hz), 2.10 (s, 3 H); IR (KBr) 3400, 1660, 1620 cm−1; MS eI m/z 412; CHN calc'd for $C_{26}H_{24}N_2O_3$+0.4 $H_2O$.

EXAMPLE 16

(E)-N,N-Dibutyl-3-{4-[5-hydroxy-2-(4-fluoro-phenyl)-3-methyl-indol-1-ylmethyl]-phenyl}-acrylamide Mp=180° C.; $^1$H NMR (DMSO) 8.77 (s, 1 H), 7.48 (d, 2 H, J=8.4 Hz), 7.41–7.38 (m, 3 H), 7.38–7.29 (m, 3 H), 7.13

(d, 1 H, J=8.8 Hz), 6.97 (d, 1 H, J=15.4 Hz), 6.85 (d, 1 H, J=2.4 Hz), 6.80 (d, 2 H, J=8.1 Hz), 5.2 (s, 2 H), 3.40–3.36 (m, 2 H), 3.30–3.27 (m, 2 H), 2.10 (s, 3 H), 1.50–1.40 (m, 4 H), 1.29–1.21 (m, H), 0.86 (t, 6 H, J=7.2 Hz); IR (KBr) 3180, 2950, 2900, 2850, 1650, 1590 cm$^{-1}$; MS eI m/z 512; CHN calcd for $C_{33}H_{37}N_2O_2$.

EXAMPLE 17

(E)-N-Butyl, N'-Methyl-3-{4-[5-hydroxy-2-(4-fluoro-phenyl)-3-methyl-indol-1-ylmethyl]-phenyl}-arylamide Mp=153–153.5° C.; $^1$H NMR (DMSO) 8.77 (s, 1 H), 7.50 (d, 2 H, J=8.1 Hz), 7.42–7.36 (m, 2 H), 7.35–7.28 (m, 3 H), 7.13 (d, 1 H, J=8.8 Hz), 7.03 (dd, 1 H, J=15.4, 2.6 Hz), 6.84 (d, 1 H, J=2.4 Hz), 6.80 (d, 2 H, J=8.1 Hz), 6.62 (dd, 1 H, J=8.8, 2.4 Hz), 5.21 (s, 2 H), 3.44, 3.41 (2 t, 2 H, J=7.0 Hz), 3.06, 2.87 (2 s, 3 H), 2.10 (s, 3 H), 1.49–1.42 (m, 2 H), 1.27–1.20 (m, 2 H), 0.86 (t, 3 H); IR (KBr) 3300, 2950, 2860, 1645, 1580 cm$^{-1}$; MS eI m/z 470; CHN calcd for $C_{30}H_{31}FN_2O_2$.

Biological Methods

In Vitro Estrogen Receptor Bonding Assay

Receptor Preparation

CHO cells overexpressing the estrogen receptor were grown in 150 mm$^2$ dishes in DMEM+10% dextran coated charcoal, stripped fetal bovine serum. The plates were washed twice with PBS and once with 10 mM Tris-HCl, pH 7.4, 1 mM EDTA. Cells were harvested by scraping the surface and then the cell suspension was placed on ice. Cells were disrupted with a hand-held motorized tissue grinder using two, 10-second bursts. The crude preparation was centrifuged at 12,000 g for 20 minutes followed by a 60 minute spin at 100,000 g to produce a ribosome free cytosol. The cytosol was then frozen and stored at −80° C. Protein concentration of the cytosol was estimated using the BCA assay with reference standard protein.

Binding Assay Conditions

The competition assay was performed in a 96-well plate (polystyrene*) which binds <2.0% of the total input [$^3$H]-17β-estradiol and each data point was gathered in triplicate. 100 uG/100 uL of the receptor preparation was aliquoted per well. A saturating dose of 2.5 nM [$^3$H]17β-estradiol+ competitor (or buffer) in a 50 uL volume was added in the preliminary competition when 100× and 500× competitor were evaluated, only 0.8 nM [$^3$H] 17β-estradiol was used. The plate was incubated at room temperature for 2.5 h. At the end of this incubation period 150 uL of ice-cold dextran coated charcoal (5% activated charcoal coated with 0.05% 69 K dextran) was added to each well and the plate was immediately centrifuged at 99 g for 5 minutes at 4° C. 200 uL of the supernatant solution was then removed for scintillation counting. Samples were counted to 2% or 10 minutes, whichever occurs first. Because polystyrene absorbs a small amount of [$^3$H]17β-estradiol, wells containing radioactivity and cytosol, but not processed with charcoal were included to quantitate amounts of available isotope. Also, wells containing radioactivity but no cytosol were processed with charcoal to estimate unremovable DPM of [$^3$H] 170β-estradiol. Corning #25880-96, 96-well plates were used because they have proven to bind the least amount of estradiol.

Analysis of Results

Counts per minute (CPM) of radioactivity were automatically converted to disintegrated per minute (DPM) by the Beckman LS 7500 Scintillation Counter using a set of quenched standards to generate a H# for each sample. To calculate the % of estrediol binding in the presence of 100 or fold 500 fold competitor the following formula was applied:

((DPM sample-DPM not removed by charcoal)/(DPM estradiol-DPM not removed by charcoal))×100%=% of estradiol binding For the generation of IC$_{50}$ curves, % binding is plotted vs compound. IC$_{50}$'s are generated for compounds that show >30% competition at 500× competitor concentration. For a description of these methods, see Hulme, E. C., ed. 1992. Receptor-Ligand Interactions: A Practical Approach. IRL Press, New York (see especially chapter 8).

Ishikawa Cell Alkaline Phosphatase Assay

Cell Maintenance and Treatment

Ishikawa cells were maintained in DMEM/F12 (50%:50%) containing phenol red+10% fetal bovine serum and the medium was supplemented with 2 mM Glutamax, 1% Pen/Strap and 1 mM sodium pyruvate. Five days prior to the beginning of each experiment (treatment of cells) the medium was changed to phenol red-free DMEM/F12+10% dextran coated charcoal stripped serum. On the day before treatment, cells were harvested using 0.5% trypsin/EDTA and plated at a density of $5\times10_4$ cells/well in 96-well tissue culture plates. Test compounds were dosed at $10^{-6}$, $10^{-7}$ and $10^{-8}$ M in addition to $10^{-6}$ M (compound)+$10^{-9}$ M 17β-estradiol to evaluate the ability of the compounds to function as antiestrogens. Cells were treated for 48 h prior to assay. Each 96-well plate contained a 17β-estradiol control. Sample population for at each dose was n=8.

Alkaline Phosphatase Assay

At the end of 48 h the media is aspirated and cells are washed three times with phosphate buffered saline (PBS). 50 µL of lysis buffer (0.1 M Tris-HCl, pH 9.8, 0.2% Triton X-100) is added to each well. Plates are placed at −80° C. for a minimum of 15 minutes. Plates are thawed at 37° C. followed by the addition of 150 µL of 0.1 M Tris-HCl, pH 9.8, containing 4 mM para-nitrophenylphosphate (pNPP) to each well (final concentration, 3 mM pNPP).

Absorbance and slope calculations were made using the KineticCalc Application program (Bio-Tek Instruments, Inc., Winooski, Vt.). Results are expressed as the mean +/−S.D. of the rate of enzyme reaction (slope) averaged over the linear portion of the kinetic reaction curve (optical density readings every 5 minutes for 30 minutes absorbance reading). Results for compounds are summarized as percent of response related to 1 nM 17β-estradiol.

Various compounds were assayed for estrogenic activity by the alkaline phosphatase method and corresponding ED50 values (95% C.I.) were calculated. The four listed in the following were used as reference standards:

| | |
|---|---|
| 17β-estradiol | 0.03 nM |
| 17α-estradiol | 1.42 nM |
| estriol | 0.13 nM |
| estrone | 0.36 nM |

A description of such methods is provided by Holinka, C. F., Hata, H., Kuramoto, H. and Gurpide, E. (1986) Effects of steroid hormones and antisteroids on alkaline phosphatase activity in human endometrial cancer cells (Ishikawa Line). Cancer Research, 46:2771–2774, and by Littlefield, B. A., Gurpide, E., Markiewicz, L., McKinley, B. and by Hochberg, R. B. (1990) A simple and sensitive microtiter plate estrogen bioassay based on stimulation alkaline phosphatase in Ishikawa cells; Estrogen action of D5 adrenal steroids. Endocrinology, 6:2757–2762.

2X VIT ERE Transfection Assay

Cell Maintenance and Treatment

Chinese Hamster Ovary cells (CHO) which had been stably transfected with the human estrogen receptor were maintained in DMEM+10% fetal bovine serum (FBS). 48 h prior to treatment the growth medium was replaced with DMEM lacking phenol red +10% dextran coated charcoal stripped FBS (treatment medium). Cells were plated at a density of 5000 cells/well in 96-well plates containing 200 µL of medium/well.

Calcium Phoshate Transfection

Reporter DNA (Promega plasmid pGL2 containing two tandem copies of the vitellogenin ERE in front of the minimal thymidine kinase promoter driving the luciferase gene) was combined with the B-galactosidase expression plasmid pCH110 (Pharmacia) and carrier DNA (pTZ18U) in the following ratio:

```
10 uG of reporter DNA
5 uG of pCH110DNA
5 uG of pTZ18U
20 uG of DNA/1 mL of transfection solution
```

The DNA (20 uG) was dissolved in 500 uL of 250 mM sterile $CaCl_2$ and added dropwise to 500 uL of 2×HeBS (0.28 M NaCl, 50 mM HEPES, 1.5 mM $Na_2HPO_4$, pH 7.05) and incubated at room temperature for 20 minutes. 20 uL of this mixture was added to each well of cells and remained on the cells for 16 h. At the end of this incubation the precipitate was removed, the cells were washed with media, fresh treatment media was replaced and the cells were treated with either vehicle, 1 nM 17β-estradiol, 1 uM compound or 1 uM compound+1 nM 17β-estradiol (tests for estrogen antagonism). Each treatment condition was performed on 8 wells (n=8) which were incubated for 24 h prior to the luciferase assay.

Luciferase Assay

After 24 h exposure to compounds, the media was removed and each well washed with 2× with 125 uL of PBS lacking $Mg^{++}$ and $Ca^{++}$. After removing the PBS, 25 uL of Promega lysis buffer was added to each well and allowed to stand at room temperature for 15 min, followed by 15 min at –80° C. and 15 min at 37° C. 20 uL of lysate was transferred to an opaque 96 well plate for luciferase activity evaluation and the remaining lysate (5 uL) was used for the B-galactosidase activity evaluation (normalize transfection). The luciferan substrate (Promega) was added in 100 uL aliquots to each well automatically by the luminometer and the light produced (relative light units) was read 10 seconds after addition.

B-Galactosidase Assay

To the remaining 5 uL of lysate 45 uL of PBS was added. Then 50 uL of Promega B-galactosidase 2× assay buffer was added, mixed well and incubated at 37° C. for 1 hour. A plate containing a standard curve (0.1 to 1.5 milliunits in triplicate) was set up for each experimental run. The plates were analyzed on a Molecular Devices spectrophotometric plate reader at 410 nm. The optical densities for the unknown were converted to milliunits of activity by mathematical extrapolation from the standard curve.

Analysis of Results

The luciferase data was generated as relative light units (RLUs) accumulated during a 10 second measurement and automatically transferred to a JMP (SAS Inc) file where background RLUs were subtracted. The B-galactosidase values were automatically imported into the file and these values were divided into the RLUs to normalize the data. The mean and standard deviations were determined from a n=8 for each treatment. Compounds activity was compared to 17β-estradiol for each plate. Percentage of activity as compared to 17β-estradiol was calculated using the formula %=((Estradiol-control)/(compound value))×100. These techniques are described by Tzukerman, M. T., Esty, A., Santiso-Mere, D., Danielian, P., Parker, M. G., Stein, R. B., Pike, J. W. and McDonnel, D. P. (1994). Human estrogen receptor transactivational capacity was determined by both cellular and promoter context and mediated by two functionally distinct intramolecular regions (see Molecular Endocrinology, 8:21–30).

Rat Uterotrophic/Antiuterotrophic Bioassay

The estrogenic and antiestrogenic properties of the compounds were determined in an immature rat uterotrophic assay (4 day) that (as described previously by L. J. Black and R. L. Goode, Life Sciences, 26, 1453 (1980)). Immature Sprague-Dawley rats (female, 18 days old) were tested in groups of six. The animals were treated by daily ip injection with 10 uG compound, 100 uG compound, (100 uG compound+1 uG 17β-estradiol) to check antiestrogenicity, and 1 uG 17β-estradiol, with 50% DMSO/50% saline as the injection vehicle. On day 4 the animals were sacrificed by $CO_2$ asphyxiation and their uteri were removed and stripped of excess lipid, any fluid removed and the wet weight determined. A small section of one horn was submitted for histology and the remainder used to isolate total RNA in order to evaluate complement component 3 gene expression.

| Biological Results Estrogen Receptor Affinity (reported as RBA: 17β-estradiol = 100) ||
|---|---|
| Compound | RBA |
| raloxifene | 200 |
| tamoxifen | 1.8 |
| Example 10 | 20 |
| Example 7 | 42 |
| Example 8 | 40 |
| Example 9 | 40 |
| Example 12 | 114 |
| Example 11 | 80 |
| Example 13 | 27 |
| Example 14 | 32 |
| Example 15 | 53 |

| Infection Luciferase Assay |||
|---|---|---|
| Compound | % Activation | % Activation with 1 nM 17β-estradiol |
| 17β-estradiol | 100% | N/A |
| estriol | 38% | N/A |
| tamoxifen | 0% | 10% |

-continued

| | | |
|---|---|---|
| raloxifene | 0% | 0% |
| Example 10 | 1% | 2% |
| Example 7 | 4% | 8% |
| Example 8 | 6% | 78% |
| Example 9 | 6% | 8% |
| Example 12 | 13% | 24% |
| Example 11 | 8% | 12% |
| Example 13 | 8% | 17% |
| Example 14 | 19% | 57% |
| Example 15 | 15% | 31% |

Ishikawa Alkaline Phosphatase Assay

| Compound | % Activation | % Activation (Compound ± 1 nM 17β-estradiol) |
|---|---|---|
| 17β-estradiol | 100% | N/A |
| tamoxifen | 0% | 45% |
| raloxifen | 5% | 5% |
| Example 10 | 6% | 19% |
| Example 7 | 1% | 9% |
| Example 8 | 10% | 22% |
| Example 9 | 3% | 11% |
| Example 12 | 7% | 16% |
| Example 11 | 6% | 11% |
| Example 13 | 7% | 9% |
| Example 14 | 2% | 14% |
| Example 15 | 0% | 5% |

3-Day Ovariectomized Rat Model

| Compound | 10 μG | 100 μG | 100 μG plus 1 μG 17β-Estradiol |
|---|---|---|---|
| Tamoxifen | | 69.6 mg | 71.4 mg |
| Raloxifen | | 47.5 mg | 43.2 mg |
| control = 42.7 mg | 1 μG 17β-estradiol = 98.2 | | |
| Example 7 | 47.8 mg | 64.8 mg | 75.4 |
| control = 20.2 mg | 1 μG 17β-estradiol = 80.2 mg | | |
| Example 12 | 36.9 mg | 49.5 mg | 63.1 |
| control = 31.4 mg | 1 μG 17β-estradiol = 89.0 mg | | |
| Example 11 | 39.3 mg | 59.8 mg | 81.0 mg |
| Control = 24.5 mg | 1 μG 17β-estradiol = 90.8 mg | | |
| Example 14 | 32.5 mg | 56.4 mg | 79.8 mg |
| Example 15 | 40.4 mg | 56.3 mg | 69.3 mg |
| control = 29.1 mg | 1 μg 17β-estradiol = 95.5 mg | | |

What is claimed:

1. A compound having the structure:

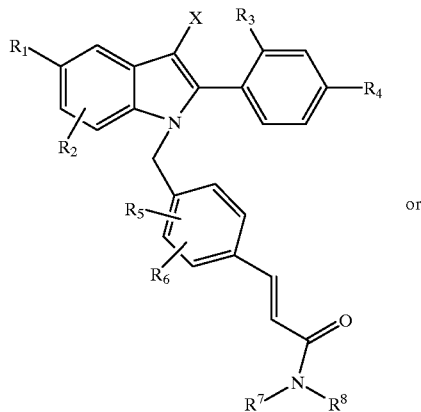

or

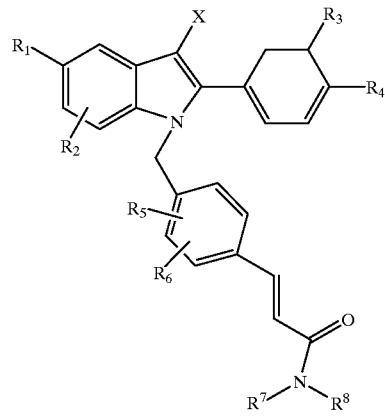

wherein:

$R_1$ is selected from H, OH or the $C_1$–$C_4$ esters or alkyl ethers thereof, or halogen;

$R_2$, $R_3$, $R_4$, $R_5$, and $R_6$ are independently selected from H, OH or the $C_1$–$C_4$ esters, or alkyl ethers thereof, halogen, cyano, $C_1$–$C_6$ alkyl or trifluoromethyl, with the proviso that, when $R_1$ is H, $R_2$ is not OH;

X is selected from H, $C_1$–$C_6$ alkyl, cyano, nitro, trifluoromethyl, halogen;

$R_7$ and $R_8$ are independently selected from the group of H, $C_1$–$C_6$ alkyl, phenyl; or a pharmaceutically acceptable salt thereof.

2. A compound of claim 1 which is (E)-N,N-Diethyl-3-{4-[5-hydroxy-2-(4-hydroxy-phenyl)-3-methyl-indol-1-ylmethyl]-phenyl}-acrylamide.

3. A compound of claim 1 which is 1(E)-N-tert-butyl-3-{4-[5-hydroxy-2-(4-hydroxy-phenyl)-3-methyl-indol-1-ylmethyl]-phenyl}-acrylamide.

4. A compound of claim 1 which is (E)-N,N-Dimethyl-3-{4-[5-hydroxy-2-(4-hydroxy-phenyl)-3-methyl-indol-1-ylmethyl]-phenyl} acrylamide.

5. A compound of claim 1 which is (E)-N,N-Dibutyl-3-{4-[5-hydroxy-2-(4-hydroxy-phenyl)-3-methyl-indol-1-ylmethyl]-phenyl}-acrylamide.

6. A compound of claim 1 which is (E)-N-Butyl, N'-methyl-3-{4-[5-hydroxy-2-(4-hydroxy-phenyl)-3-methyl-indol-1-ylmethyl]-phenyl}-acrylamide.

7. A compound of claim 1 which is (E)-3-{4-[5-hydroxy-2-(4-hydroxy-phenyl)-3-methyl-indol-1-ylmethyl]-phenyl}-acrylamide.

8. A compound of claim 1 which is (E) N,Methyl-3-{4-[5-hydroxy-2-(4-hydroxy-phenyl)-3-methyl-indol-1-ylmethyl]-phenyl}-acrylamide.

9. A compound of claim 1 which is (E)-N,N-Dibutyl-3-{-4-[5-hydroxy-2-(4-fluoro-phenyl)-3-methyl-indol-1-ylmethyl]-phenyl}-acrylamide.

10. A compound of claim 1 which is (E)-N-Butyl, N'-Methyl-3-{4-[5-hydroxy-2-(4-fluoro-phenyl)-3-methyl-indol-1-ylmethyl]-phenyl}-acrylamide.

11. A pharmaceutical composition comprising a compound of claim 1, or a pharmaceutically acceptable salt thereof, and a pharmaceutically acceptable carrier or excipient.

12. A method of treating or preventing bone loss in a mammal, the method comprising administering to a mammal in need thereof an effective amount of compound of claim 1, or a pharmaceutically acceptable salt thereof.

13. A method of treating or preventing disease states or syndromes which are caused or associated with an estrogen deficiency in a mammal, the method comprising administering to a mammal in need thereof an effective amount of a compound of claim 1, or a pharmaceutically acceptable salt thereof.

14. A method of treating or preventing cardiovascular disease in a mammal, the method comprising administering to a mammal in need thereof an effective amount of a compound of claim 1, or a pharmaceutically acceptable salt thereof.

* * * * *